United States Patent
Walling et al.

(10) Patent No.: US 12,318,605 B2
(45) Date of Patent: *Jun. 3, 2025

(54) IMPLANTABLE DEVICE MIGRATION CONTROL

(71) Applicant: Cochlear Limited, Macquarie University (AU)

(72) Inventors: Grahame Walling, Macquarie University (AU); James G. E. Smith, Macquarie University (AU); Julia Mitchell, Macquarie University (AU); Krishna Sivaraman, Macquarie University (AU); Graeme Vincent, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1001 days.

This patent is subject to a terminal disclaimer.

(21) Appl. No.: 17/368,951

(22) Filed: Jul. 7, 2021

(65) Prior Publication Data

US 2021/0330964 A1   Oct. 28, 2021

Related U.S. Application Data

(63) Continuation of application No. 14/632,543, filed on Feb. 26, 2015, now Pat. No. 11,090,484, which is a continuation of application No. 13/712,384, filed on Dec. 12, 2012, now abandoned.

(51) Int. Cl.
*A61N 1/05* (2006.01)
*A61N 1/36* (2006.01)
*A61N 1/375* (2006.01)

(52) U.S. Cl.
CPC ........... *A61N 1/0541* (2013.01); *A61N 1/375* (2013.01); *A61N 1/36038* (2017.08); *A61N 1/3758* (2013.01)

(58) Field of Classification Search
CPC .... A61N 1/05; A61N 1/0541; A61N 1/36038; A61N 1/375; A61N 1/3758
See application file for complete search history.

(56) References Cited

U.S. PATENT DOCUMENTS

| 5,906,634 | A | 5/1999 | Flynn et al. |
| 7,212,864 | B2 | 5/2007 | Wahlstand et al. |
| 7,396,265 | B2 | 7/2008 | Darley et al. |
| 7,937,156 | B2 | 5/2011 | Gibson |
| 7,988,507 | B2 | 8/2011 | Darley et al. |
| 7,996,982 | B2 | 8/2011 | Parley et al. |
| 8,145,314 | B2 | 3/2012 | McDonald |

(Continued)

FOREIGN PATENT DOCUMENTS

| EP | 0705621 | 4/1996 |
| WO | 2007053882 | 5/2007 |

*Primary Examiner* — Christopher A Flory
(74) *Attorney, Agent, or Firm* — Edell, Shapiro & Finnan, LLC

(57) ABSTRACT

Devices and methods are disclosed for a stimulator unit in a medical device, such as an implantable component of a cochlear implant. In embodiments, the stimulator unit comprises a bottom wall configured to be substantially contacting a temporal bone of a recipient, and a top wall positioned opposite the bottom wall, wherein a cross section of the stimulator unit has an outer profile substantially parallel to the bottom wall and the top wall.

19 Claims, 13 Drawing Sheets

(56) References Cited

U.S. PATENT DOCUMENTS

| | | | |
|---|---|---|---|
| 8,277,227 B2 | 10/2012 | Darley et al. | |
| 8,515,540 B2 | 8/2013 | Eigh et al. | |
| 2002/0038136 A1* | 3/2002 | Zaouali | A61N 1/37512 607/36 |
| 2003/0109903 A1 | 6/2003 | Berrage et al. | |
| 2004/0173221 A1 | 9/2004 | Singhal et al. | |
| 2004/0176814 A1 | 9/2004 | Singhal et al. | |
| 2005/0003268 A1* | 1/2005 | Scott | A61N 1/37518 607/116 |
| 2005/0159791 A1 | 7/2005 | Daly et al. | |
| 2006/0116743 A1 | 6/2006 | Gibson et al. | |
| 2009/0005835 A1 | 1/2009 | Greenberg et al. | |
| 2009/0034769 A1 | 2/2009 | Darley et al. | |
| 2009/0048580 A1* | 2/2009 | Gibson | A61F 11/00 607/57 |
| 2009/0209806 A1 | 8/2009 | Hakansson | |
| 2010/0137929 A1 | 6/2010 | Libbey et al. | |
| 2011/0190833 A1 | 8/2011 | Ries et al. | |
| 2011/0257503 A1* | 10/2011 | Mehdizadeh | A61N 1/3752 600/393 |
| 2011/0266713 A1* | 11/2011 | Vincent | B29C 45/14754 264/255 |
| 2012/0012374 A1 | 1/2012 | Koester et al. | |
| 2012/0123497 A1 | 5/2012 | Sherva et al. | |
| 2012/0123502 A1* | 5/2012 | Aghassian | A61N 1/025 607/59 |
| 2012/0221078 A1* | 8/2012 | Leigh | A61N 1/36038 607/57 |
| 2012/0306128 A1 | 12/2012 | Parker et al. | |
| 2014/0046416 A1* | 2/2014 | Bennett | A61N 1/0502 607/116 |
| 2014/0163626 A1 | 6/2014 | Walling et al. | |
| 2016/0218444 A1* | 7/2016 | King, Jr. | H01R 4/2454 |

\* cited by examiner

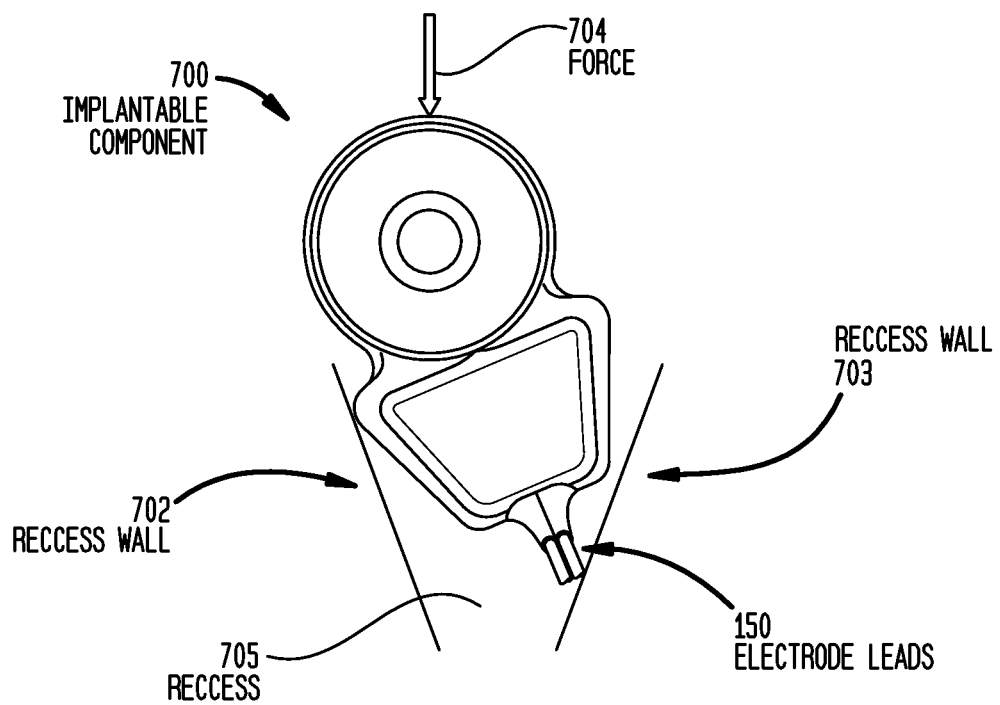
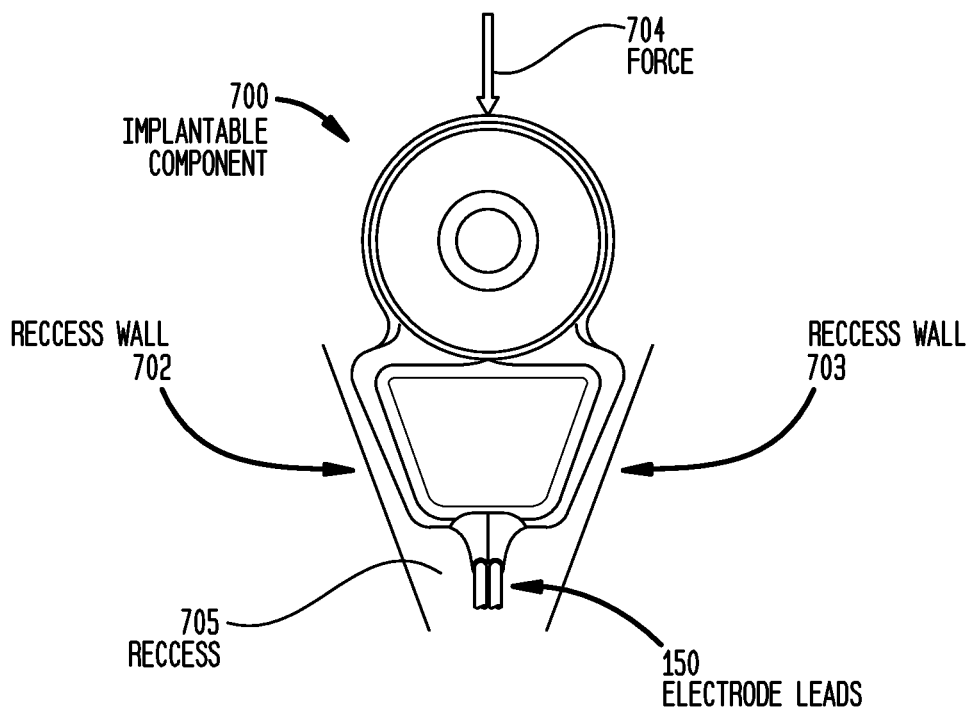

IMPLANTABLE DEVICE MIGRATION CONTROL

BACKGROUND

Field of the Invention

The present technology relates generally to implantable components of medical devices, and more particularly, to controlling the migration of such implantable components.

Related Art

The use of medical devices to provide therapy to individuals for various medical conditions has become more widespread as the therapeutic benefits of such devices become more widely appreciated and accepted throughout the population. For example, hearing aids, implantable pacemakers, defibrillators, functional electrical stimulation devices, prosthetic hearing devices, organ assist and replacement devices, drug delivery devices and other medical devices, have successfully performed lifesaving, lifestyle enhancement or other therapeutic functions for many individuals.

The type of implantable medical devices and the range of functions performed thereby have increased over the years. For example, many such implantable medical devices often include one or more instruments, apparatus, sensors, processors, controllers or other functional mechanical, electrical or electronic components that are permanently or temporarily implanted in a patient to perform diagnosis, prevention, monitoring, treatment or management of a disease or injury or symptom thereof, or to investigate, replace or modify of the anatomy or of a physiological process. Many of these implantable components receive power and/or data from external components that are part of, or operate in conjunction with, the implantable component.

Hearing loss, which may be due to many different causes, is generally of two types, conductive and sensorineural. In some cases, a person suffers from both types of hearing loss. Conductive hearing loss occurs when the normal mechanical pathways for sound to reach the cochlea are impeded, for example, by damage to the ossicles. Individuals suffering from conductive hearing loss typically have some form of residual hearing because the hair cells in the cochlea are undamaged. As a result, individuals suffering from conductive hearing loss typically receive a prosthetic hearing device that generates mechanical motion of the cochlea fluid. For example, acoustic energy may be delivered through a column of air to the tympanic membrane (eardrum) via a hearing aid residing in the ear canal. Mechanical energy may be delivered via the physical coupling of a mechanical transducer (i.e. a transducer that converts electrical signals to mechanical motion) to the tympanic membrane, the skull, the ossicular chain, the round or oval window of the cochlea or other structure that will result in the delivery of mechanical energy to the hydro-mechanical system of the cochlea.

In many people who are profoundly deaf, however, the reason for their deafness is sensorineural hearing loss. Sensorineural hearing loss occurs when there is damage to the inner ear, or to the nerve pathways from the inner ear to the brain. As such, many individuals suffering from sensorineural hearing loss are unable to derive suitable benefit from prosthetic hearing devices that provide acoustical or mechanical stimulation. As a result, prosthetic hearing devices that deliver electrical stimulation to nerve cells of the recipient's auditory system have been developed. Electrically-stimulating prosthetic hearing devices include, for example, auditory brain stimulators and cochlear prostheses.

As described above, oftentimes sensorineural hearing loss is due to the absence or destruction of the cochlear hair cells which transduce acoustic signals into nerve impulses. Cochlear implants provide a recipient with a hearing percept by delivering electrical stimulation signals directly to the auditory nerve cells, thereby bypassing absent or defective hair cells that normally transduce acoustic vibrations into neural activity. Such devices generally use a stimulating assembly implanted in the cochlea so that the electrode contacts may differentially activate auditory neurons that normally encode differential pitches of sound. As is known in the art, a stimulating assembly comprises a plurality of electrode contacts each individually electrically connected to a stimulator unit via elongate conductive elements, such as wires.

SUMMARY

In one aspect of the present technology there is provided a stimulator unit of an implantable device, comprising: a bottom wall configured to be substantially contacting a temporal bone of a recipient; and a top wall positioned opposite to the bottom wall; wherein a cross section of the stimulator unit is substantially parallel to the bottom wall and the top wall.

In another aspect there is provided a method of implanting a stimulator unit of an implantable device in a recipient, comprising: implanting a first guide post into a temporal bone of the recipient; implanting a second guide post into the temporal bone of the recipient; forming a recess into the temporal bone of the recipient in between the first guide post and the second guide post; implanting a stimulator unit into the recess, wherein the stimulator unit comprises a first side wall and a second side wall, wherein the first side wall and second side wall are tapered towards one end of the stimulator unit; wherein the first guide post contacts the first side wall, and wherein the second guide post contacts the second side wall.

In another aspect there is provided a method for implanting an implantable component adjacent to a skull of a recipient, wherein the implantable component may travel along a migration path subsequent to implantation, the method comprising: forming a recess into the temporal bone of the recipient wherein the recess includes a first guide and a second guide; and implanting a housing, tapered in a plane parallel to a surface of the skull, into the recess; wherein the housing contacts the first guide and the second guide, and wherein the first guide and the second guide are configured to prevent migration of the housing.

BRIEF DESCRIPTION OF THE DRAWINGS

Embodiments of the present technology are described below with reference to the attached drawings, in which:

FIG. 7A illustrates a misaligned implant in a V-shaped boney recess, in accordance with embodiments of the present technology;

FIG. 7B illustrates an aligned implant in a V-shaped boney recess, in accordance with embodiments of the present technology;

DETAILED DESCRIPTION

Cochlear implants generally include a stimulating assembly implanted in the cochlea to deliver electrical stimulation signals to the auditory nerve cells, thereby bypassing absent or defective hair cells. The electrode contacts of the stimulating assembly differentially activate auditory neurons that normally encode differential pitches of sound. This assembly enables the brain to perceive a hearing sensation resembling the natural hearing sensation normally perceived by the human brain.

The receiver/stimulator unit is implanted in the head of the recipient by drilling a recess into the mastoid region of the temporal bone. Therefore, the mastoid cavity, drilled by the surgeon, and the lead connections between the stimulator unit and other components of the cochlear implant, such as the internal coil and elongate stimulating assembly, are dependent on the shape of the receiver/stimulator unit. Embodiments of the present technology utilize a stimulator unit that has a tapered, trapezoidal, wedge, triangle, of diamond shape, for example. The boney recess drilled for implantation of such an implantable device may be contoured to match the shape of the device.

Figure 1:
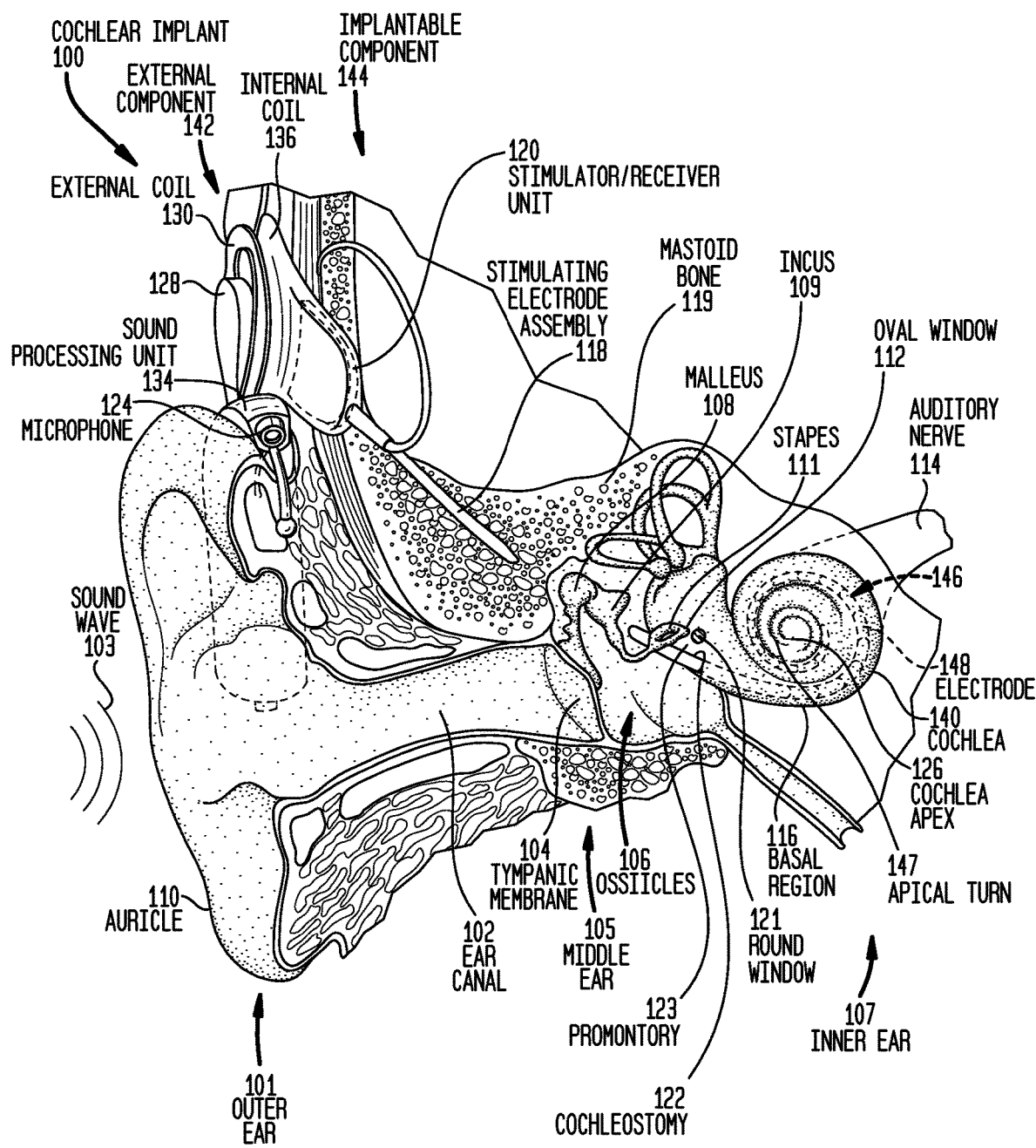
FIG. 1 illustrates a perspective view of a cochlear implant in which embodiments of the present technology may be implemented.

FIG. 1 is perspective view of a cochlear implant, referred to as cochlear implant 100, implanted in a recipient. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window/fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises an external component 142 which is directly or indirectly attached to the body of the recipient, and an internal or implantable component 144 which is temporarily or permanently implanted in the recipient. External component 142 may comprise one or more functional components which generate to receive data. For example, in the exemplary arrangement of FIG. 1, external component 142 comprises one or more sound input elements, shown as microphone 124 for detecting sound, and a sound processing unit 126. Sound processing unit 126 converts the sound received by microphone 124 into encoded data signals. As described in detail below, sound processing unit 126 may comprise a transmitter unit which transmits the encoded data signals to an internal receiver unit 132 in internal component 144. Also as described in greater detail below, in certain embodiments of the present technology, implantable component 144 may process the sound received by microphone 124. In such embodiments, the electrical signals output by microphone 124 are transmitted to implantable receiver unit 132.

External component 142 further comprises a charging module 128 configured to provide power to implantable component 144. As described in detail below, charging module 128 comprises a power source (not shown), a power transmitter (also not shown), an external coil 130, and, preferably, a magnet (also not shown) secured directly or indirectly to external coil 130. The power transmitter use external coil 130 to transmit power to internal component 144.

In certain examples, external coil 130 transmits electrical signals (e.g., power and stimulation data) to internal coil 136 via a radio frequency (RF) link, as noted above. Various types of energy transfer, such as infrared (IR), electromagnetic, capacitive and inductive transfer, may be used to transfer the power and/or data from external device to cochlear implant.

Implantable component 144 comprises an internal receiver/transceiver unit 132, a stimulator/receiver unit 120, and an elongate stimulating electrode assembly 118. Receiver unit 132 may be positioned in a shallow boney recess adjacent to the auricle 110 of the recipient. As detailed below, receiver unit 132 receives power and data via radio frequency (RF) links from external component 142. Receiver unit 132 comprises an internal coil 136, and preferably, a magnet (also not shown) fixed relative to the internal coil. The magnets facilitate the operational alignment of the external and internal coils, enabling internal coil 136 to receive power and stimulation data from external coil 130. Internal coil 136 is typically a wire antenna coil comprised of multiple turns of electrically insulated single-strand or multi-strand platinum or gold wire. The electrical insulation of internal coil 136 is provided by a flexible silicone molding (not shown).

Implantable component 144 further comprises a stimulator/receiver unit 120 and an elongate electrode assembly 118. Internal receiver unit 132 and stimulator/receiver unit 120 are hermetically sealed within a biocompatible housing, sometimes collectively referred to as a stimulator/receiver unit 120. Elongate electrode assembly 118 has a proximal end connected to stimulator/receiver unit 120, and a distal end implanted in cochlea 140. Electrode assembly 118 extends from stimulator/receiver unit 120 to cochlea 140 through temporal bone 119. Electrode assembly 118 is inserted or implanted into cochlea 140. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, promontory 123 or through an apical turn 147 of cochlea 140.

Electrode assembly 118 comprises a longitudinally aligned and distally extending array 146 of electrode contacts 148, sometimes referred to as electrode array 146 herein, integrated into assembly 118 along a length thereof. Stimulator/receiver unit 120 generates stimulation signals which are applied by electrode contacts 148 to cochlea 140, thereby stimulating auditory nerve 114.

FIGS. 2A-2G (collectively "FIG. 2") illustrate alternate views of one of the implantable components illustrated in FIG. 1, namely stimulator/receiver unit 120. Stimulator/receiver unit 120 comprises internal coil 136, coil lead 221, and stimulator 240. Stimulator/receiver unit 120 may comprise other components not shown, including receiver circuitry from receiver unit 132 and other components. Stimulator/receiver unit 120 has a housing 225. Stimulator/receiver unit housing 225 may have a protective casing 238 to protect leads running along housing 225. Stimulator/receiver unit housing 225 and protective casing 238 may have an overmoulding 237, which is described in more detail below. Internal coil 136 is electrically connected to internal receiver unit 132 via coil lead 221. Electrode leads 150 connect stimulator/receiver unit 120 to electrode assembly 118, which is inserted or implanted into cochlea 140.

Stimulator housing 225 comprises two surfaces: top surface 201 and bottom surface 210, four walls 202, 203, 204, 205 and four corners 206, 207, 208, 209. Top surface 201 and bottom surface 210 are spaced apart from each other. Top surface 201 and bottom surface 210 are generally substantially parallel to each other, but may not be parallel in some embodiments of the present technology. For example, top surface 201 may be curved and therefore may be concave or convex with respect to bottom surface 210.

Stimulator housing 225 may be formed of a single piece of metal or other type of material, or may be formed of two or more integrated pieces. For example, stimulator housing 225 may be formed of two integrated pieces, a first piece comprising top surface 201 and portions of side walls, for example, 202, 203, 204, 205 and a second piece comprising the bottom surface 210 and portions of the side walls. The two pieces may integrate to form one structure and may couple somewhere in the middle of the side walls or may couple at the intersection of either the top or bottom surface.

Walls 202, 203, 204, 205 are each between top surface 201 and bottom surface 210. Walls 202, 203, 204, 205 each join top surface 201 and bottom surface 210. Walls 202, 203, 204, 205 each connect top surface 201 and bottom surface 210 to each other. For example, wall 202 is contiguous with both top surface 201 and bottom surface 210. Wall 202 joins top surface 201 at edge 211 and joins bottom surface 210 at edge 212. Wall 203 is also contiguous with both top surface 201 and bottom surface 210. Wall 203 joins top surface 201 at edge 213 and joins bottom surface 210 at edge 214. Wall 204 is also contiguous with both top surface 201 and bottom surface 210. Wall 204 joins top surface 201 at edge 215 and joins bottom surface 210 at edge 216. Wall 205 is also contiguous with both top surface 201 and bottom surface 210. Wall 205 joins top surface 201 at edge 217. Each of walls 202, 203, 204, 205 that join top surface 201 and/or bottom surface 210 are continuous with that surface since edges 211, 212, 213, 214, 215, 216 (described further below) are rounded.

As shown in FIG. 2, edges 211, 212, 213, 214, 215, 216, 217 are each rounded. Implantable component 200 is implanted in the skull of the recipient by drilling a recess into the temporal bone. Therefore, after implantation, edges 211, 212, 213, 214, 215, 216, 217 will come into contact with various internal structures (bone, tissue, etc.) of the recipient's head, including the temporal bone, tissue and skin. If the corners of stimulator housing 225 were pointed or sharp, the corners contacting the head may cause pressure points in the skin or other parts of the head that can restrict blood flow. Such pressure points may cause tissue damage and/or necrosis. Furthermore, pointed or sharp corners may have a negative impact on the surgeon performing the implantation. For example, the surgeon's gloves or other surgery devices may catch on the pointed or sharp corners of the implant, which may cause the gloves or other devices to tear and expose the recipient to bacteria from the surgeon's body or elsewhere.

Because edges 211, 212, 213, 214, 215, 216, 217 may be rounded and are not necessarily sharp or defined, the edges may still comprise outer limits that define the "edges" of the surfaces and walls of stimulator housing 225. However, walls 201, 202, 203, 204 may rather be considered to be continuations of top surface 201 and bottom surface 210. In such an embodiment, stimulator housing 225 may not have four distinct "walls," but rather may simply have two surfaces that connect with each other via curved edges.

The four walls of stimulator housing 225 are generally not perpendicular to top surface 201 or bottom surface 210. Instead, walls 202, 203, 204, 205 are generally slanted upward and inward towards the center of top surface 201, and are generally slanted downward and outward towards the center of bottom surface 210, as shown in FIG. 2. In other words, walls 202, 203, 204, 205 generally form acute angles with bottom surface 210 and form obtuse angles with top surface 201. Therefore, as shown in FIG. 2, top surface 201 generally has a smaller surface area than bottom surface 210. However, in some embodiments of the present technology, the four walls of stimulator housing 225 may be perpendicular to top surface 201 or bottom surface 210. Furthermore, in other embodiments of the present technology, the four walls of stimulator housing 225 may slant in different directions with respect to top surface 201 and bottom surface 210.

As noted, stimulator housing 225 also comprises four corners 206, 207, 208, 209. Wall 202 and wall 205 are contiguous and meet to form corner 206. Wall 202 and wall 203 are contiguous and meet to form corner 207. Wall 203 and wall 204 are contiguous and meet to form corner 208. Wall 204 and wall 205 are contiguous and meet to form corner 209. In some embodiments of the present technology, contiguous walls of stimulator housing 225 are not perpendicular with each other. Instead, the angles formed by corner 206 and corner 209 are acute. Furthermore, the angles formed by corner 207 and corner 208 are obtuse. Therefore, corners 206, 207, 208, 209 form stimulator housing 225 with two surfaces, top surface 201 and bottom surface 210, that may each have a trapezoidal footprint. In other words, the outer profile or perimeter of top surface 201 and bottom surface 210 are tapered, and therefore are substantially in the shape of a trapezoid or a "wedge." The outer profile may also have the shape of a triangle, diamond, or other shape with two opposite non-parallel sides/edges. As such, edges 213 and 214 are shorter than edge 217. Furthermore, edges 213, 214 are substantially parallel to edge 217. On the other hand, edges 211, 212 are generally not parallel to edges 215, 216.

As illustrated by FIG. 2, corners 206, 207, 208, 209 are each rounded, as mentioned above, to prevent damage to other structures in the recipient's head.

Figure 2A:
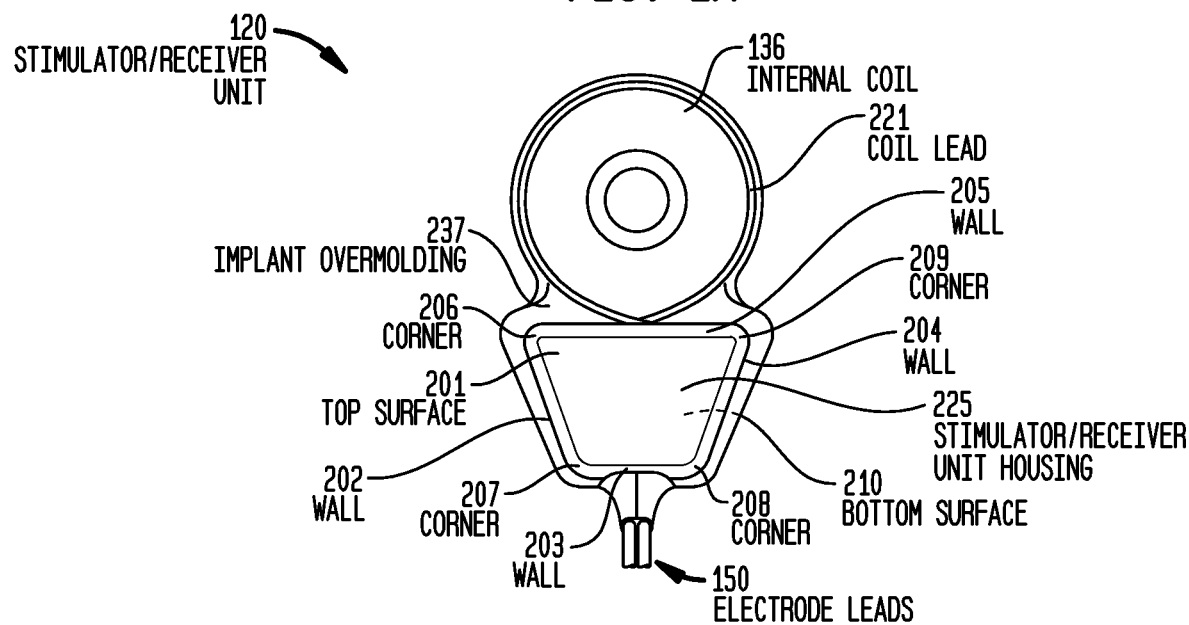
FIG. 2A illustrates a top view of an implantable device, including a stimulator unit housing, in accordance with embodiments of the present technology.
Figure 2B:
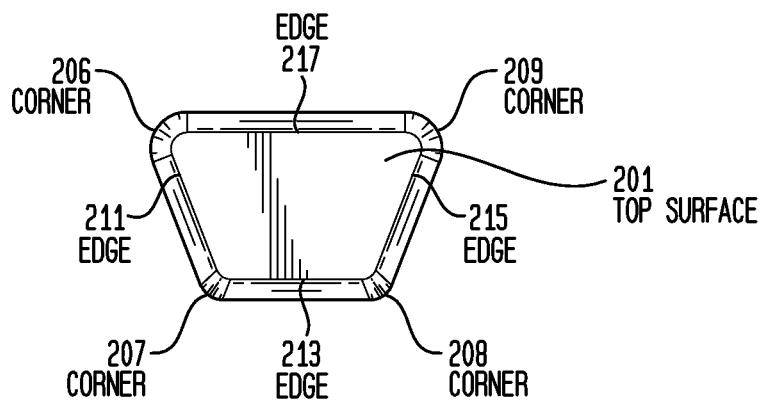
FIG. 2B illustrates an overhead view of a footprint of the top surface of a stimulator housing, in accordance with embodiments of the present technology.
Figure 2C:
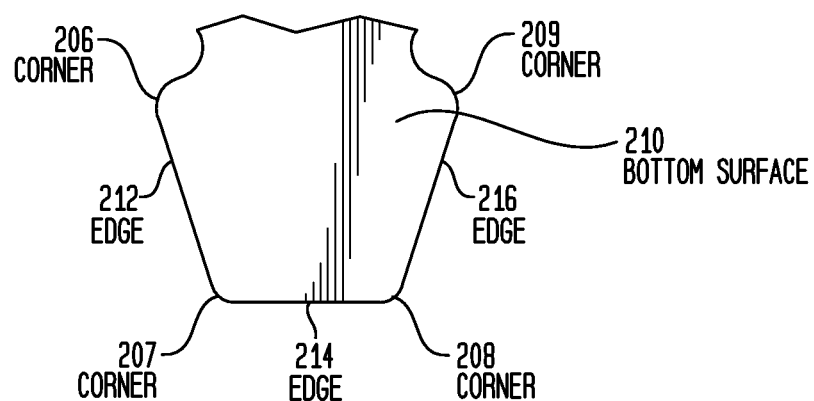
FIG. 2C illustrates a profile view of a footprint of the bottom surface of a stimulator housing, in accordance with embodiments of the present technology.
Figure 2D:
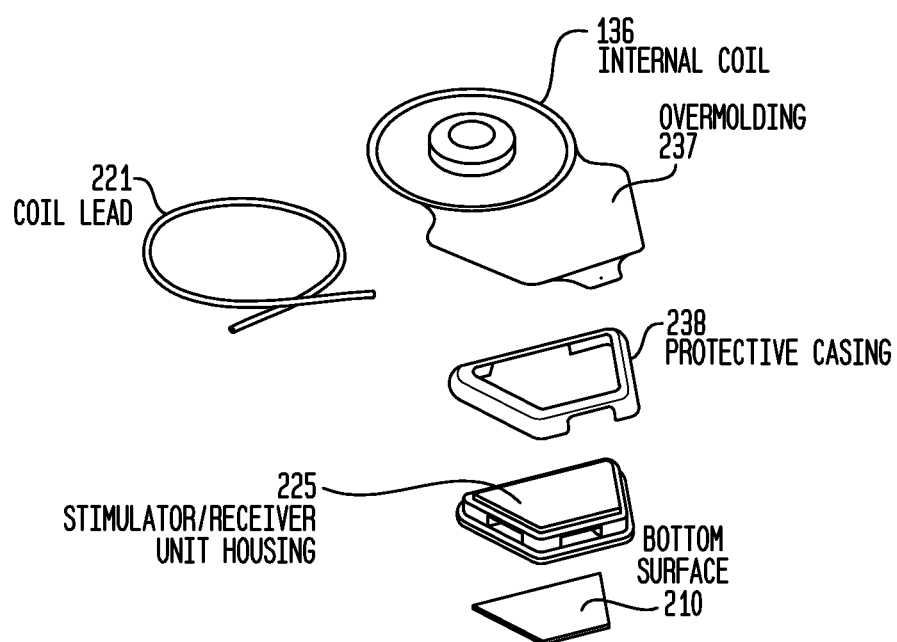
FIG. 2D illustrates an exploded view of an implantable device, in accordance with embodiments of the present technology.
Figure 2E:
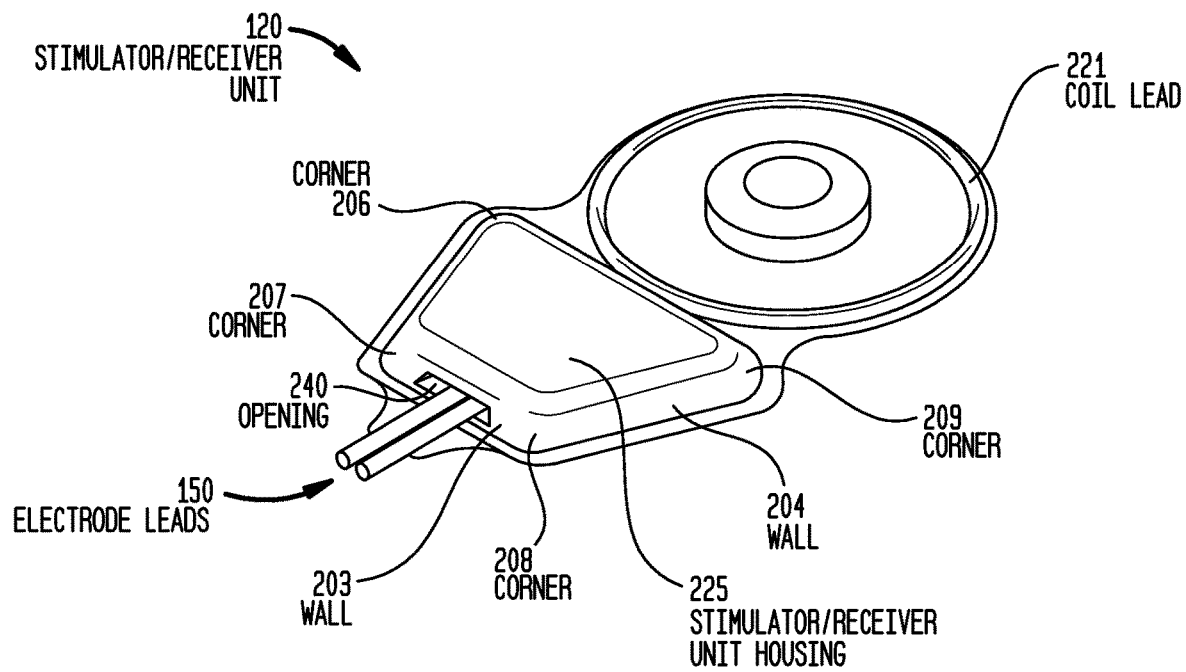
FIG. 2E illustrates an isometric view of an implantable device, in accordance with embodiments of the present technology shown in FIG. 2A.
Figure 2F:
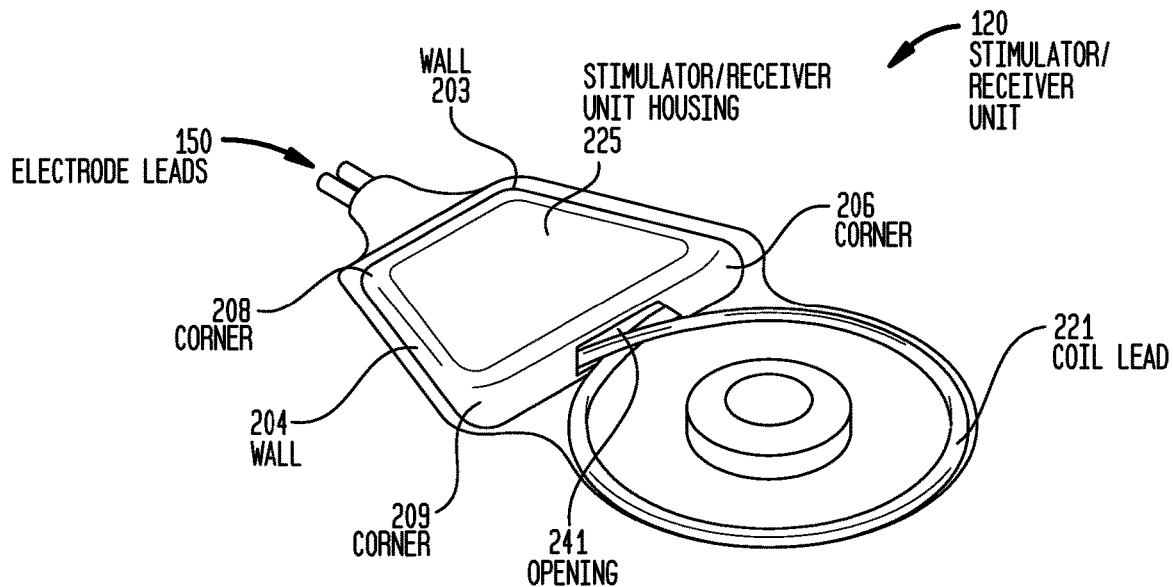
FIG. 2F illustrates a reverse isometric view of an implantable device, in accordance with embodiments of the present technology shown in FIG. 2A.
Figure 2G:
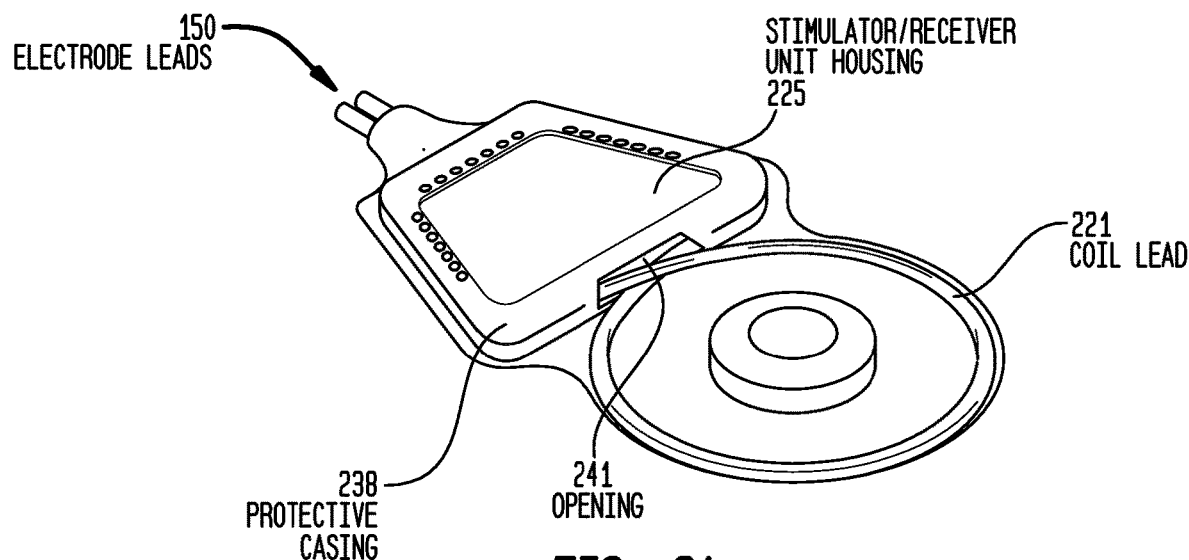
FIG. 2G illustrates an underside isometric view of an implantable device, in accordance with embodiments of the present technology shown in FIG. 2A.

Stimulator housing 225, internal coil 136 and coil lead 221 are covered and hermetically sealed by implant overmoulding 237. Overmoulding 237 protects stimulator housing 225, stimulator/receiver unit 120 and electrode leads 150, which exit stimulator housing 225 to connect to electrode assembly 118, from impact. Overmoulding 237 also seals implantable component 144 from liquid and other elements from the recipient's body that may short circuit or otherwise damage the cochlear implant. Therefore, overmoulding 237 is mostly continuous across stimulator housing 225, internal coil 136 and other elements of implantable component 200. However, overmoulding 237 may not be continuous, for example, at walls 203, 205. As shown in FIG. 2F, overmoulding 237 comprises opening or aperture 240 for electrode leads 150, which connect to stimulator/receiver unit 120 and exit stimulator housing 225 to connect to electrode assembly 118. As shown in FIG. 2E, overmoulding 237 comprises aperture 241 for coil leads 221, which connect to internal coil 136 and enter stimulator housing 225 to connect to stimulator unit 110.

Figure 3A:
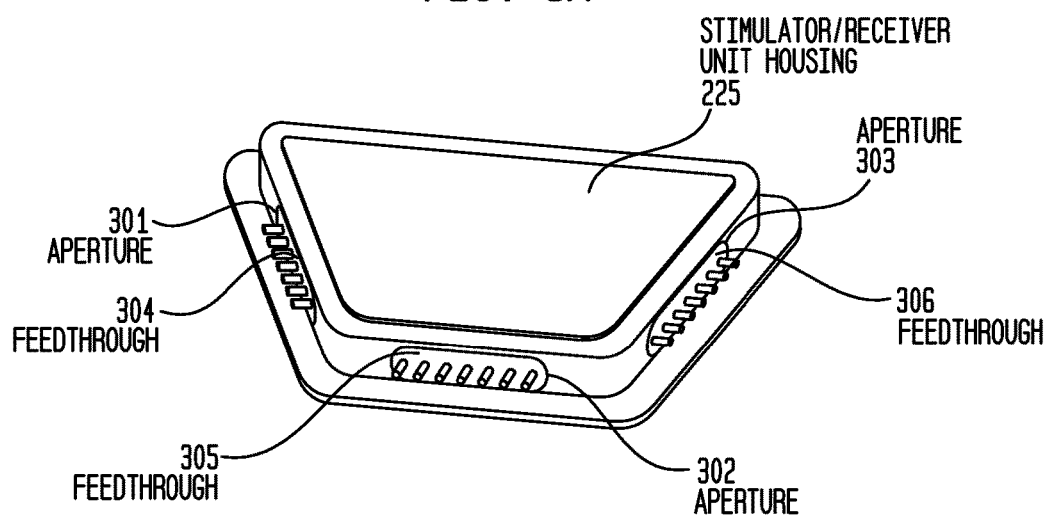
FIG. 3A illustrates a stimulator housing with feedthroughs disposed into apertures of the stimulator unit housing walls, in accordance with embodiments of the present technology.
Figure 3B:
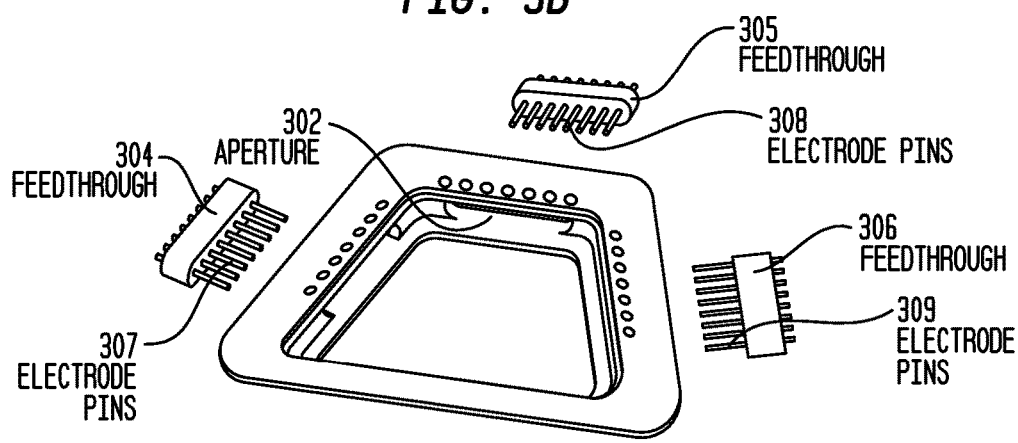
FIG. 3B illustrates an underside exploded view of a stimulator housing and feedthroughs, in accordance with embodiments of the present technology.
Figure 3C:
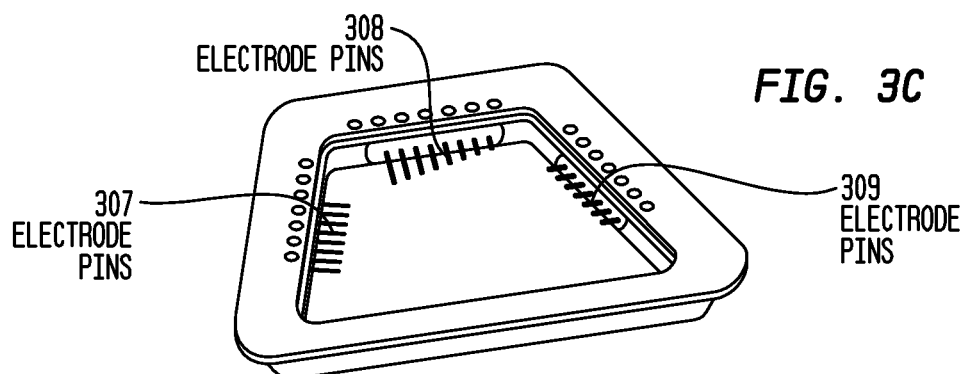
FIG. 3C illustrates an underside isometric view of a stimulator housing with feedthroughs disposed into apertures of the stimulator unit housing walls and PCB, in accordance with embodiments of the present technology.
Figure 3D:
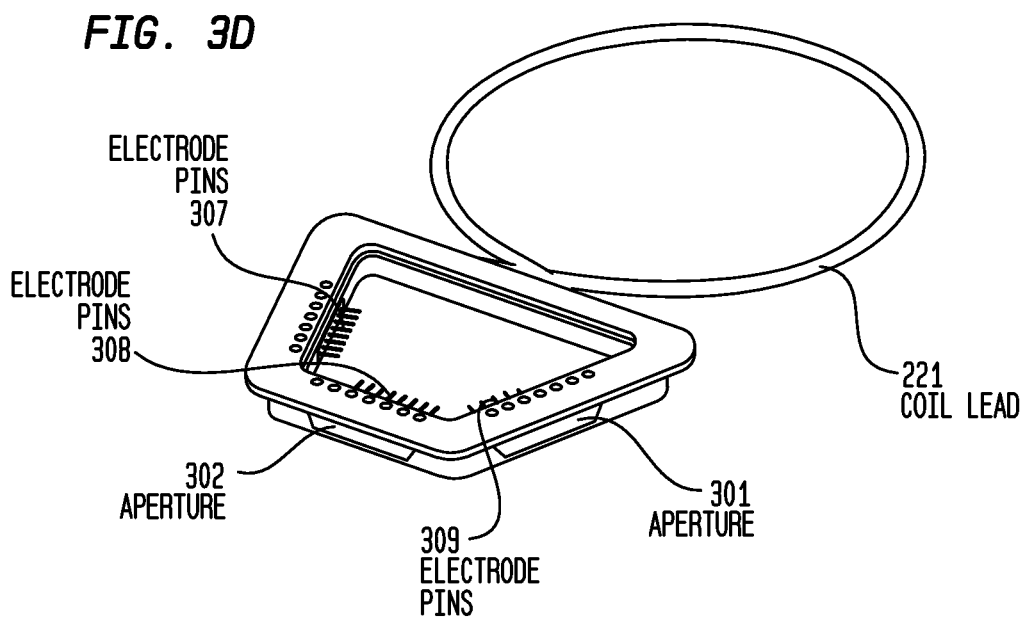
FIG. 3D illustrates underside isometric view of the stimulator housing in accordance with embodiments of the present technology as shown in FIG. 3C with coil leads attached to the stimulator unit housing.

FIG. 3A illustrates stimulator/receiver housing 225 with feedthroughs disposed in apertures of the stimulator unit housing walls, in accordance with embodiments of the present technology. FIG. 3A illustrates stimulator housing 225 without implant overmoulding 237 deposited on the top of stimulator housing 225. Stimulator housing 225 comprises aperture 301 in wall 202, aperture 302 in wall 203 and aperture 303 in wall 204. Feedthroughs 304, 305, 306 are disposed in apertures 301, 302, 303, respectively, as illustrated by FIG. 3B. FIG. 3C illustrates the underside of stimulator housing 225 with feedthroughs 304, 305 and 306 disposed into apertures 301, 302, 303. However, bottom surface 210 has been removed from the underside of stimulator housing 225 in FIG. 3C to show the internal components to stimulator housing 225. FIG. 3D illustrates a top view of the underside of stimulator housing 225 and coil lead 221 connected to stimulator housing 225. Feedthrough 304 includes electrode pin set 307, feedthrough 305 includes electrode pin set 308, and feedthrough 306 includes electrode pin set 309. When disposed into apertures 301, 302, 303 in stimulator housing 225, feedthroughs 304, 305, 306 electrically connect to a printed circuit board or other conductive pathways within stimulator housing 225 via electrode pin sets 307, 308, 309.

Apertures 301, 302, 303 are shaped such that feedthroughs 304, 305, 306 may slide into the apertures on their sides, as shown in FIG. 3B. Since apertures 301, 302, 303 are located inside walls 202, 203, 204, the feedthroughs become part of the structure of stimulator housing 225. In other words, the combination of the feedthroughs and stimulator housing 225 does not have a larger outer profile than the stimulator housing by itself. Furthermore, feedthroughs 304, 305, 306 may be disposed into apertures 301, 302, 303 so that the back end of the feedthroughs (the ends not connected to electrode pins 307, 308, 309) are flush with walls 202, 203, 204, respectively. Therefore, stimulator housing 225, including disposed feedthroughs 304, 305, 306, does not require a larger mastoid cavity for disposition into the recipient than does the stimulator housing by itself. If, on the other hand, the feedthroughs were disposed into the top of the stimulator housing, the thickness (top to bottom) of the implantable component would increase. Inserting feedthroughs into apertures of stimulator housing 225 that are in walls of stimulator housing 225 allows for the feedthroughs to embed within stimulator housing 225 while still allowing stimulator housing 225 to have access to the electrode pins 307, 308, 309 within the feedthroughs. Furthermore, if the feedthroughs were not flush with walls 202, 203, 204, the width of the implantable component would increase, causing the implantable component to take up unnecessary space in the mastoid region of the temporal bone of the recipient.

The placement of feedthroughs 304, 305, 306 also allows the electrode leads sent to electrode contacts to be trifurcated into three different groups or bunches. For example, if an electrode assembly is utilizing a set of twenty-four electrode contacts, the signal sent to those electrode contacts by stimulator/receiver unit 120 may be divided up into three sets of eight electrode contacts per group. The trifurcation of electrode leads within implantable component 200 allows for easier lead sorting. Furthermore, trifurcation of electrode leads prevents one-third of the leads, namely the leads electrically connected to feedthrough 305, from being bent or wrapped around a corner at all, which further prevents possible damage to those leads.

The location of feedthroughs 304, 305, 306, within the body of stimulator housing 225, also allows the feedthroughs to act as stiffening members under the chassis walls of stimulator housing 225. If implantable component 200 were impacted while implanted in the recipient's head (such as, for example, a child hitting the implanted portion of its head against the ground, causing the ground to impact at least top surface 201 of stimulator housing 225), the impact resistance structure would consist of both stimulator housing 225 and feedthroughs 304, 305, 306. Feedthroughs 304, 305, 306 provide additional hard material to resist impact and protect stimulator housing 225 and its contents from the same.

Figure 3E:
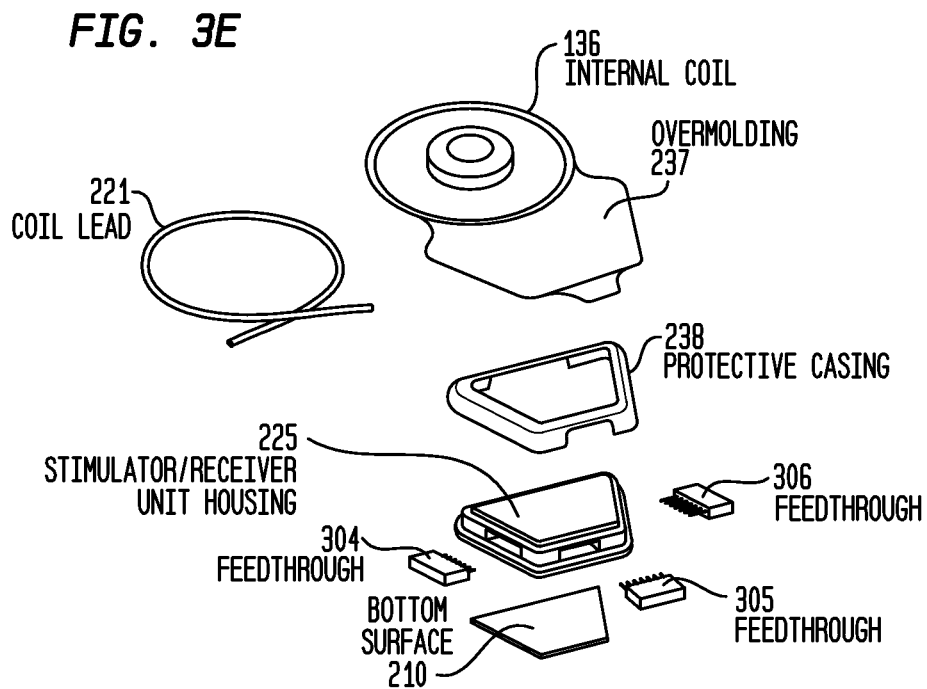
FIG. 3E illustrates an exploded view of an implantable device with feedthroughs, in accordance with embodiments of the present technology.

FIG. 3E illustrates a "blown up" version of implantable component 200, including stimulator housing 225, feedthroughs 304, 305, 306, internal coil 136, overmoulding 237, coil lead 221 and the contents of stimulator housing 225.

Although FIGS. 3A-3F show stimulator housing 225 with only three apertures and three feedthroughs, according to alternative embodiments of the present technology, fewer or additional apertures and feedthroughs may be utilized. Furthermore, if implantable component 200 of FIGS. 3A-3F is covered with overmoulding such as overmoulding 237, the overmoulding covering walls 203 and 205 would include apertures for electrode leads 150 to connect to electrode assembly 118 and for coil leads 221 to connect to internal coil 136.

Figure 4A:
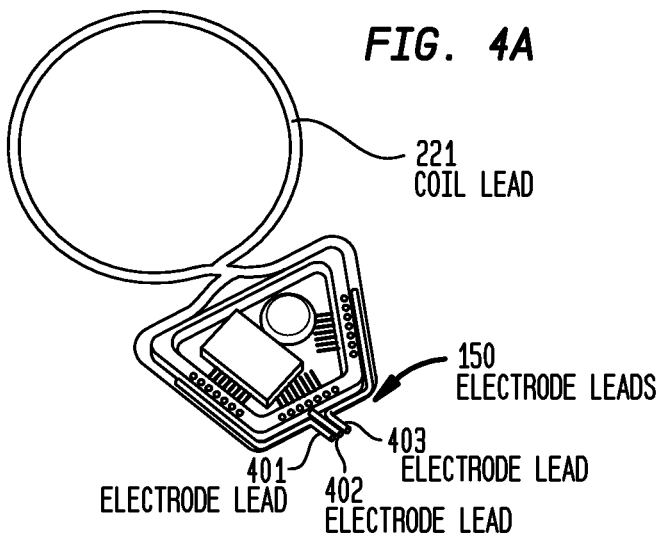
FIG. 4A illustrates an isometric view of electrode lead routing from three feedthroughs of a stimulator unit housing, in accordance with embodiments of the present technology.
Figure 4B:
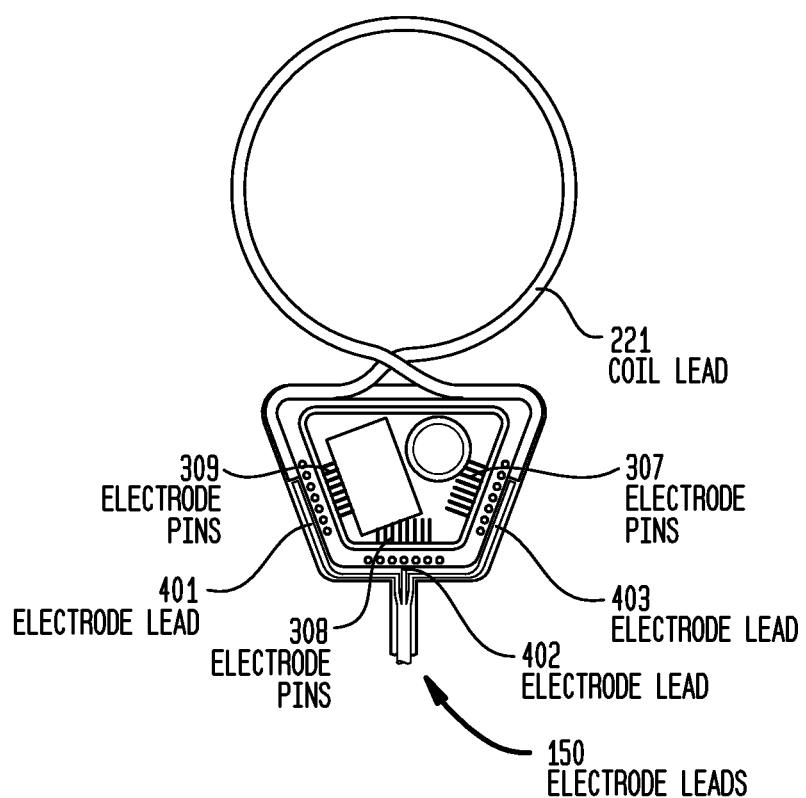
FIG. 4B illustrates a top view of electrode lead routing from three feedthroughs of a stimulator unit housing, in accordance with embodiments of the present technology.

FIGS. 4A and 4B (collectively, FIG. 4) illustrates alternative views of electrode lead routing from three feedthroughs of a stimulator unit housing, in accordance with embodiments of the present technology. More specifically, FIGS. 4A and 4B illustrate embodiments of the present technology including routing of electrode leads 150 to connect feedthroughs 304, 305, 306 with a component external to stimulator housing 225, such as stimulating electrode assembly 118. Electrode leads 150 include, in embodiments of the present technology, three electrode leads 401, 402 and 403. Electrode lead 401 connects on one end of feedthrough 304, electrode lead 402 connects on one end of feedthrough 305, and electrode lead 403 connects on one end of feedthrough 306. After exiting feedthrough 304, electrode lead 401 follows wall 202 of stimulator housing 225 towards corner 207. When electrode lead 401 reaches corner 207, electrode lead 401 wraps around corner 207 and follows wall 203 until the lead reaches the portion of wall 203 that includes aperture 302 in wall 203. After exiting feedthrough 306, electrode lead 403 follows wall 204 of stimulator housing 225 towards corner 208. When electrode lead 403 reaches corner 208, electrode lead 403 wraps around corner 208 and follows wall 203 until the lead reaches the portion of wall 203 that includes aperture 302 in wall 203. Electrode lead 402 exits aperture 302 directly from feedthrough 305 and at an angle normal to wall 203. Electrode leads 401, 402 and 403 join each other along wall 203 at or near aperture 302 and feedthrough 305. Electrode leads 401, 402 and 403 then exit stimulator housing 225 to connect to electrode assembly 118. Trifurcation of leads, as noted, allows for simple lead sorting, and also allows for electrode leads 150 to be routed out of stimulator housing 225 in parallel as one main electrode bundle.

The tapered or trapezoidal/wedge shape of stimulator housing 225 allows electrode leads 150 to run along the outside of stimulator housing 225 without taking up additional space in the recipient's head. As noted above, feedthroughs 304, 305 and 306 are disposed into apertures 301, 302 and 303, respectively, of stimulator housing 225 so that the back end of the feedthroughs are substantially flush with walls 202, 203 and 204, respectively, so that the width of the implantable component does not increase due to the feedthroughs. Similarly, because walls 202 and 204 are not perpendicular to wall 203, and instead form a stimulator housing 225 that has a trapezoidal shape, electrode leads exiting stimulator housing 225 will not add to the largest overall width of implantable component 200. In other words, because wall 205 is longer than wall 203, electrode leads 150 may exit the apertures in stimulator housing 225 and follow walls 202 and 204 without extending outwards from implantable component 200 beyond the ends of wall 205 (which, according to embodiments of the present technology, has the greatest width of any portion of implantable component 200).

As noted above and as illustrated by FIG. 2, corners 206, 207, 208, 209 are rounded according to embodiments of the present technology. After implantation of implantable component 200 into the recipient's head, corners 206, 207, 208, 209 will come into contact with various internal portions of the recipient's head, including the temporal bone, tissue and skin. If the corners of stimulator housing 225 were acute, pointed or sharp, the corners contacting the head may, for example, cause pressure points in the skin or other parts of the head that can restrict blood flow. As also noted, electrode leads 401 and 403 wrap around corners 207 and 208, respectively. If the corners of stimulator housing 225 were acute, pointed or sharp, the corners contacting electrode leads 401 and 403 may, for example, cause pressure points in the electrode leads. Such pressure points may cause the leads to break or otherwise damage, causing the electronic elements of the implantable component to short circuit or otherwise not work properly. The embodiments illustrated in FIGS. 4A and 4B maximize linear pathways for electrode leads 150 and minimize their contact with right angled or acute corners.

Figure 5A:
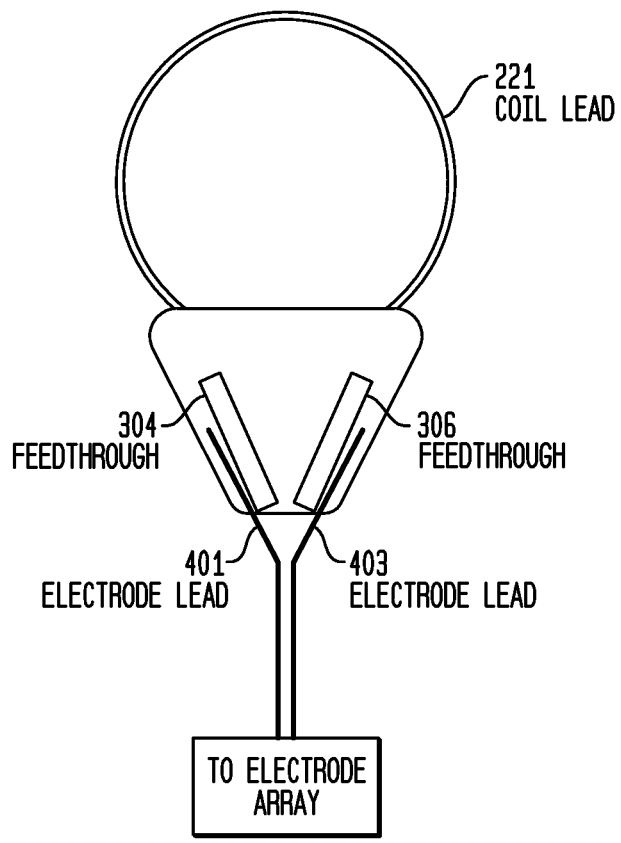
FIG. 5A illustrates a top view of v-shaped electrode lead routing from two feedthroughs of a stimulator unit housing, in accordance with embodiments of the present technology.
Figure 5B:
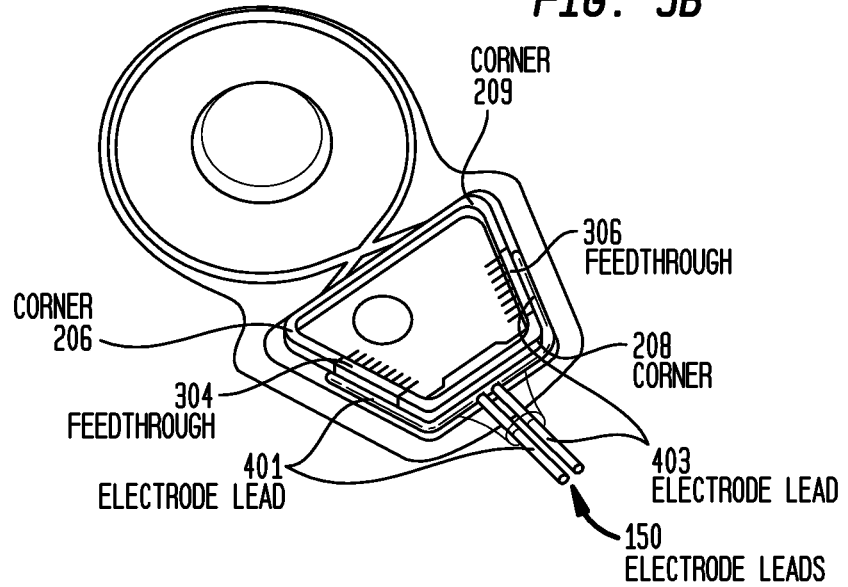
FIG. 5B illustrates an isometric view of electrode lead routing from two feedthroughs of a stimulator unit housing, in accordance with embodiments of the present technology.

FIGS. 5A and 5B (collectively, FIG. 5) illustrate alternative views of v-shaped electrode lead routing from two feedthroughs of a stimulator unit housing, in accordance with embodiments of the present technology. More specifically, FIGS. 5A and 5B illustrate a two feedthrough variant of the electrode lead routing system of FIG. 4. As shown, for example, in FIG. 5A, stimulator housing 225 only includes two feedthroughs 304 and 306. Similar to FIG. 4, electrode lead 401 connects on one end to feedthrough 304 and electrode lead 403 connects on one end to feedthrough 306. After exiting feedthrough 304, electrode lead 401 follows wall 202 of stimulator housing 225 towards corner 207. When electrode lead 401 reaches corner 207, electrode lead 401 wraps around corner 207 and follows wall 203 until the lead reaches the center portion of wall 203. After exiting feedthrough 306, electrode lead 403 follows wall 204 of stimulator housing 225 towards corner 208. When electrode lead 403 reaches corner 208, electrode lead 403 wraps around corner 208 and follows wall 203 until the lead reaches the center portion of wall 203. Electrode leads 401 and 403 join each other along wall 203. Electrode leads 401 and 403 then exit stimulator housing 225 to connect to electrode assembly 118. Alternatively, as illustrated in FIG. 5A, electrode lead 401 may not wrap around corner 207 and electrode lead 403 may not wrap around corner 208. Instead, electrode lead 401 may follow wall 202 of stimulator housing 225 and past corner 207 and electrode lead 403 may follow wall 204 of stimulator housing 225 and past corner 208 until electrode leads 402 and 403 join together away from wall 203 before connecting with electrode assembly 118.

Referring back to FIG. 3E, additional components may be disposed within implantable component 200. For example, a layer of protective casing 311 may be deposited on top of stimulator housing 225. Specifically, protective casing 311 may cover only portions of stimulator housing 225, such as the portions of stimulator housing 225 above feedthroughs 304, 305, 306 and electrode leads 401, 402, 403. Protective casing 311 may protect the components of implantable component 200 from impact or from liquid or other elements from inside the recipient's head. Overmoulding 237 may be placed on top of protective casing 311 to protect stimulator housing 225, stimulator/receiver unit 120 and other contents of stimulator housing 225 and may further protect and electrode leads 401, 402, 403 from impact and other foreign elements.

Figure 6A:
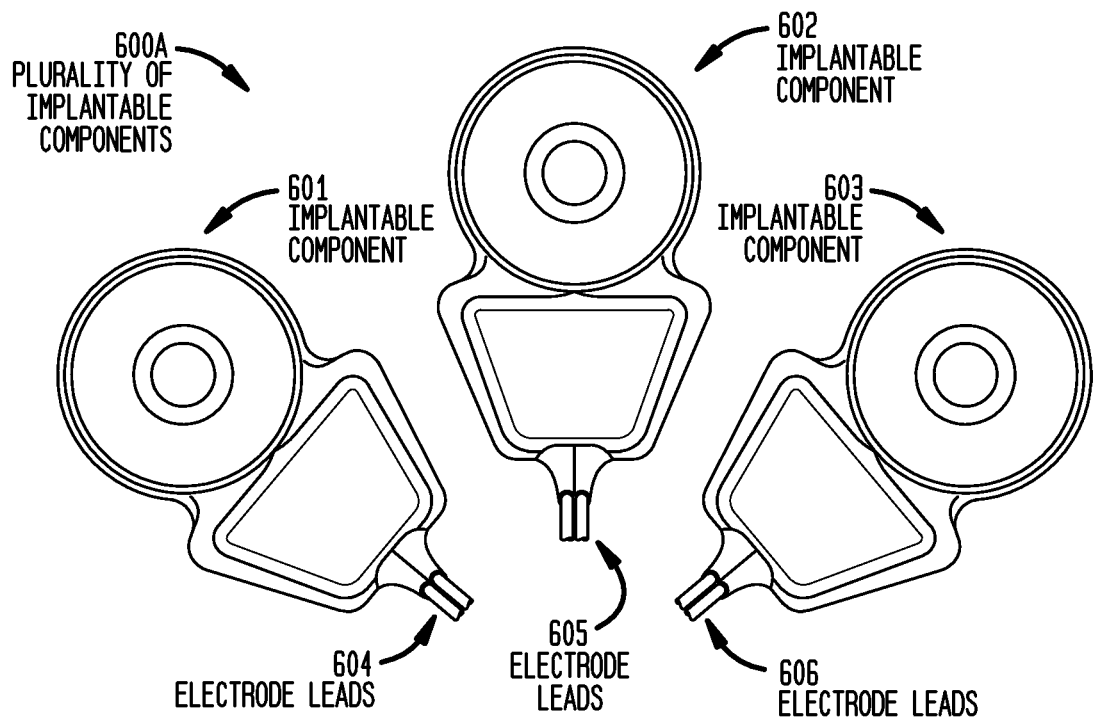
FIG. 6A illustrates a fanned arrangement of devices, in accordance with embodiments of the present technology.
Figure 6B:
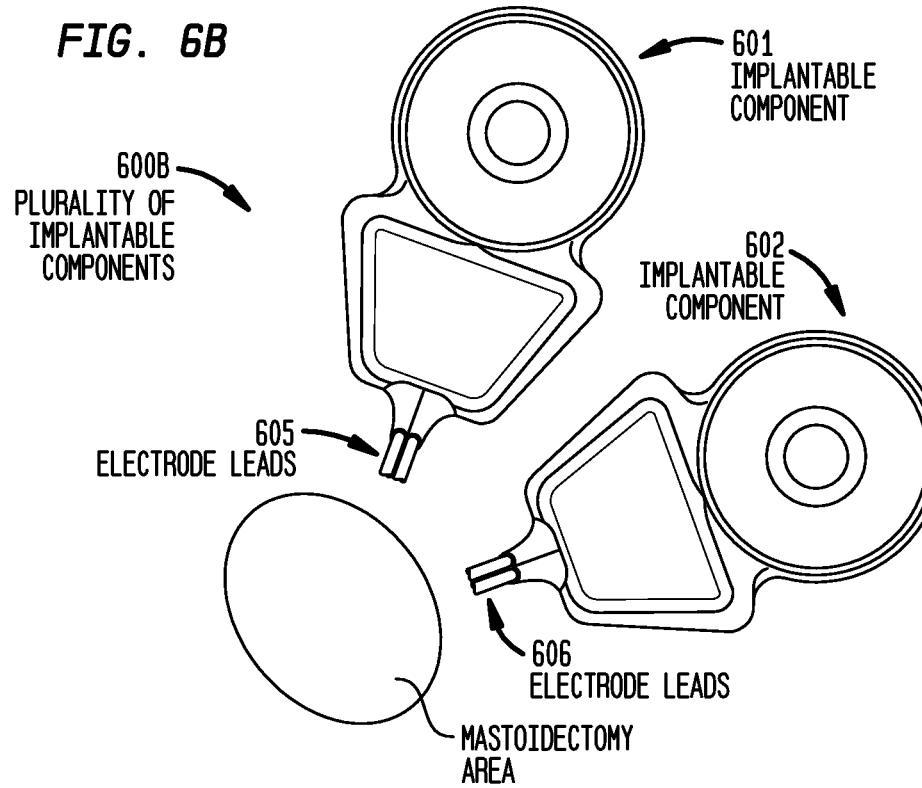
FIG. 6B illustrates a fanned arrangement of devices relative to the mastoidectomy, in accordance with embodiments of the present technology.

FIGS. 6A and 6B (collectively, FIG. 6) illustrate a fanned arrangement of implantable devices, in accordance with embodiments of the present technology. More specifically, FIGS. 6A and 6B illustrate the implantation of multiple implantable components in the head of a recipient. For example, as illustrated in FIG. 6A, a plurality of implantable components 600A includes three or more implantable components 601, 602, 603 that may be implanted in a recipient's head in a fanned arrangement such that a side wall one implantable component is placed next to and parallel to a side wall of another implantable component. The placement of implantable components in such a fanned arrangement allows for close packing of multiple implantable components, including a minimized implementation or drilled recess area for surgery. Such a fanned arrangement also allows for a more efficient connection between the multiple implantable components while using shorter electrode leads. Because of the fanned arrangement of implantable components 601, 602, 603, electrode leads 604, 605 and 606 are close together. Shorter leads spaced closely together helps to protect the connection between the implantable components and between the implantable components and an electrode array. FIG. 6B illustrates the implantation of multiple implantable components in the head of a recipient with respect to a mastoidectomy. For example, FIG. 6B shows plurality of implantable components 600A that includes two or more implantable components 601 and 602 in a fanned arrangement with electrode leads 605, 606 leading to a mastoidectomy area.

Figure 8A:
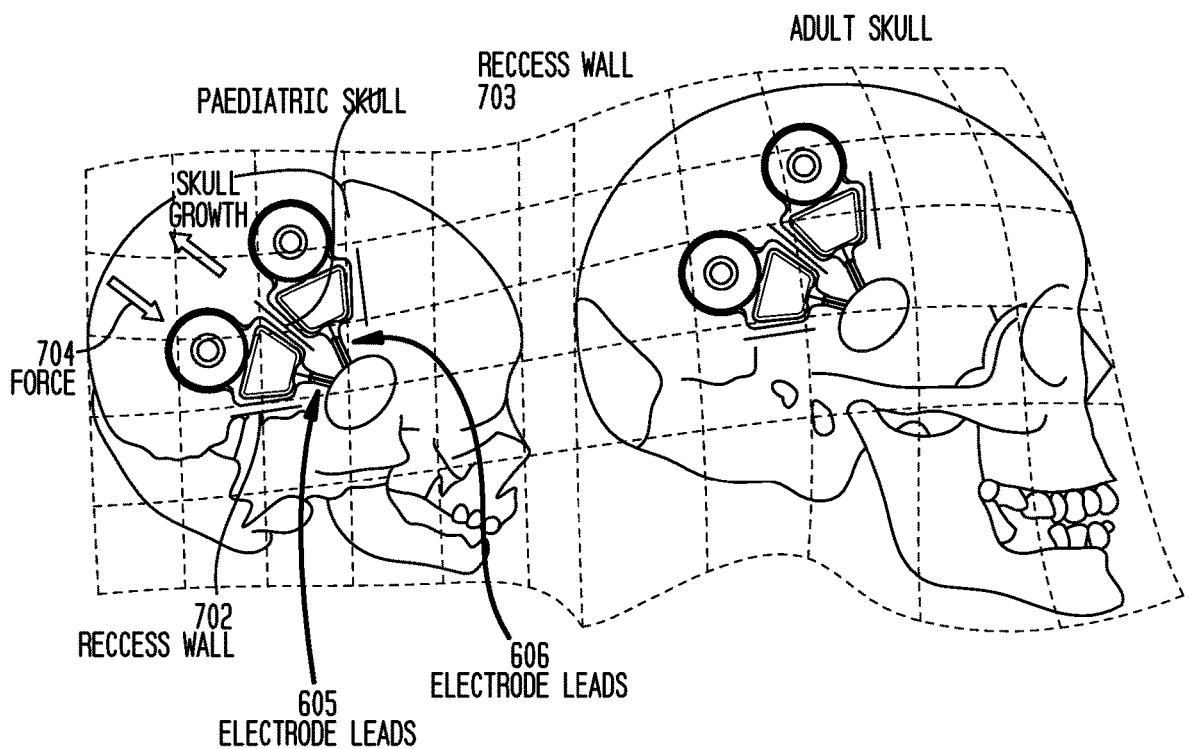
FIG. 8A illustrates the direction of growth of skull bones, in accordance with embodiments of the present technology.
Figure 8B:
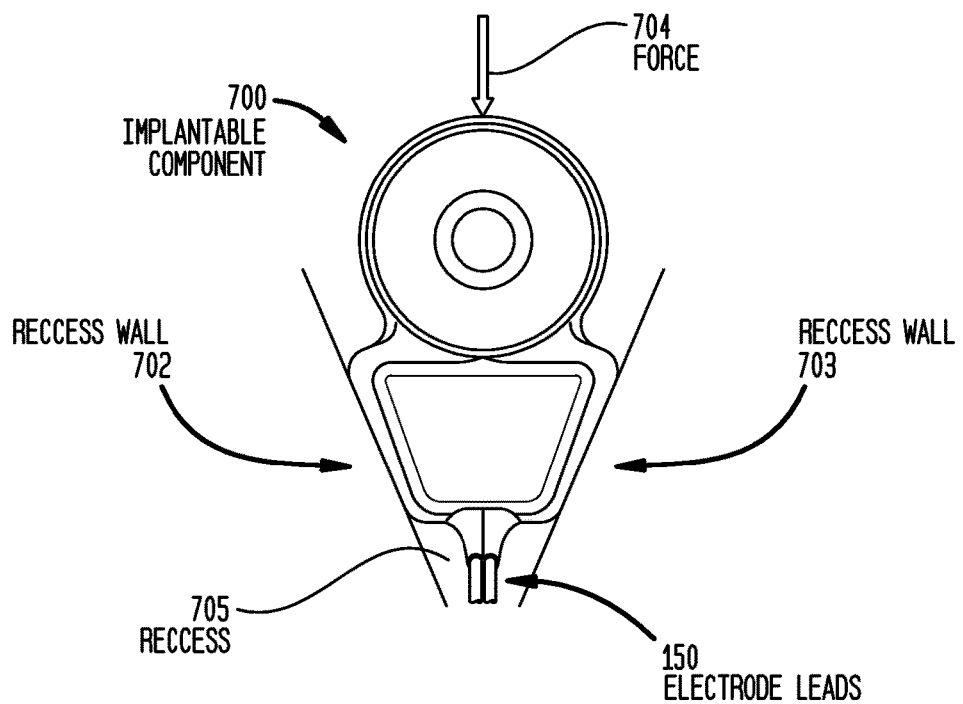
FIG. 8B illustrates walls of an aligned implant in a V-shaped boney recess pressed against walls of the recess, in accordance with embodiments of the present technology.

FIGS. 7A and 7B (collectively, FIG. 7) illustrate the contrast between possible alignments of implantable component 200 with trapezoidal shaped stimulator housing 225 within a boney recess. More specifically, FIGS. 7A and 7B illustrate a diagram of an exemplary V-shaped well or recess 705 that is drilled into a recipient's head/bone for implantation of implantable component 200. FIG. 7A illustrates stimulator housing 225 mis-aligned within recess 705, according to embodiments of the present technology. After an implant is implanted within the head of a recipient, the implant may shift over time due to growth of the recipient's skull/cranial bones, impact applied to the recipient's head, or other factors. FIG. 8 illustrates the direction of growth of skull bones, in accordance with embodiments of the present technology. As shown in FIG. 8A, growth of the human skull may cause force 704 on implantable component 200 in a direction towards the front of the recipient's head, or towards the tapered or narrow portion of V-shaped recess 705. As force 704 is applied to implantable component 200, implantable component 200 self-aligns to orient itself within the boney recess, as shown in FIG. 7B. As more and more force is applied to implantable component 200 over time (or, in other words, as force 704 continues to be applied for a longer and longer period of time), implantable component 200 will become further wedged against walls 702 and 703 of recess 705, as shown in FIG. 8B. Walls 702 and 703 of boney recess 705 form boundaries for the implantation's surgery site. Walls 702 and 703, therefore, help guide implantable component 200 as the recipient's skull grows and as implantable component 200 attempts to shift or migrate over time. It is beneficial for implantable component 200 to be wedged inside recess 705 as deeply as possible so that the implantable component is as secure as possible within the periosteal pocket and will not migrate to different portions of the recipient's head.

Boney recess 705 may have a ramped floor, or implant seat. In other words boney recess 705 may be deeper in certain portions of the boney recess than others. More specifically, as recess 705 becomes deeper, the height of the sidewalls of recess 705 may increase. Ramped recess 705 helps prevent accidental migration of implantable component 200 away from the mastoidectomy. Migration of implantable component 200, whether along the surface of the recipient's head or in a direction normal to the recipient's head, may put unnecessary stress on electrode leads 150. Such stress on electrode leads 150 may cause electrode leads 150 to break or otherwise damage implantable component 200, such as stimulator/receiver unit 120, connected to the leads. Stress on electrode leads 150 may also damage the implantation of electrode assembly 118 implanted inside the cochlea of the recipient. Such stress may cause electrode assembly 118 to become dislodged from the recipient's cochlea or damage the cochlea itself.

Figure 9A:
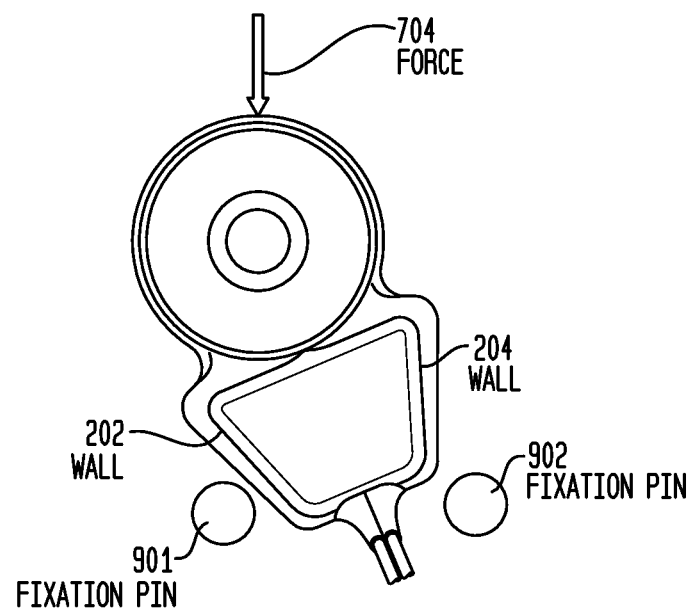
FIG. 9A illustrates a mis-aligned implant in between two fixation pins in a boney recess, in accordance with embodiments of the present technology.
Figure 9B:
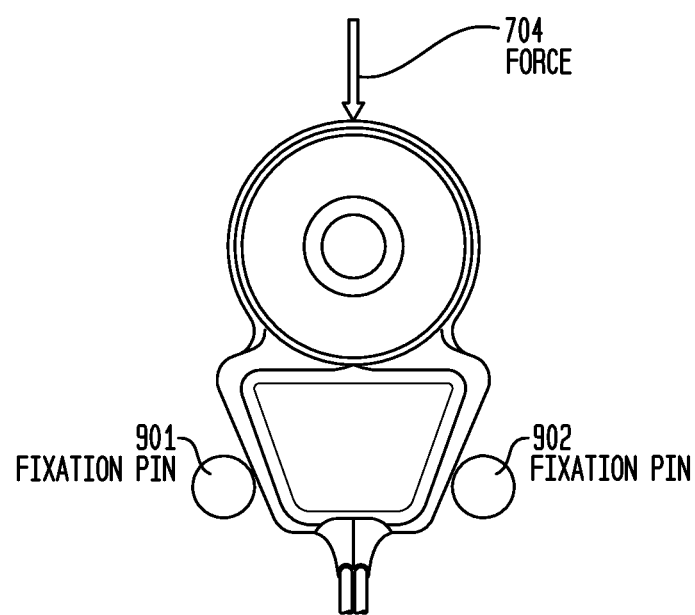
FIGS. 9B illustrates an aligned implant in between two fixation pins in a boney recess, in accordance with embodiments of the present technology.

FIGS. 9A and 9B (collectively, FIG. 9) illustrate an exemplary method of implementing embodiments of the present technology. More specifically, FIG. 9 illustrates implantable component 200 implanted within fixation guides/pins 901 and 902. Fixation guides 901 and 902 may be pins, studs, screws or other similar medical devices. As shown in FIG. 9, pins 901 and 902 are implanted into the boney bone of the recipient. The distance between implanted pins 901 and 902 should be the same or similar to the distance between the midpoints of the length of walls 202 and 204. The surgeon performing the implantation surgery of the implantable component then inserts implantable component 200 in between pins 901 and 902 so that walls 202 and 204 of stimulator housing 225 touch pins 901 and 902, respectively. After an implant is implanted within the head of a recipient, the implant may shift over time. As force 704 is applied to implantable component 200, implantable component 200 interacts with pins 901 and 902 and self-aligns to orient itself within the periosteal pocket and pins 901 and 902, as shown in FIG. 9B. As more and more force is applied to implantable component 200 over time (or, in other words, as force 704 continues to be applied for a longer and longer period of time), implantable component 200 will become further wedged against pins 901 and 902. Pins 901 and 902 form boundaries for the implantation's surgery site. Pins 901 and 902 help guide implantable component 200 as the recipient's skull grows and as implantable component 200 attempts to shift or migrate over time.

Pins 901, 902 also help to prevent migration of implantable component 200. Migration of implantable component 200 after implantation, whether along the surface of the recipient's head or in a direction normal to the recipient's head, would put unnecessary stress on electrode leads 150. Such stress on electrode leads 150 may cause electrode leads 150 to break or otherwise damage implantable component 200, such as stimulator/receiver unit 120, connected to the leads. Stress on electrode leads 150 may also damage the implantation of electrode assembly 118 implanted inside the cochlea of the recipient. Such stress may cause electrode assembly 118 to become dislodged from the recipient's cochlea or damage the cochlea.

Because of the tapered side walls and trapezoidal or wedge shape of stimulator housing 225 and force 704 applied by boney recess 705, only two pins are necessary to hold implantable component 200 in place. Furthermore, only two pins are necessary to allow implantable component 200 to self-align and orient itself with pins 901 and 902, and to prevent implantable component 200 from migrating. For example, if implantable component 200, and more specifically stimulator housing 225, had a rectangular shape, three or more pins would be required to hold implantable component 200 in place, to allow implantable component 200 to self-align, and to prevent implantable component 200 from migrating. In that example, one pin would be required for each of sides 202, 203, 204.

Figure 10A:
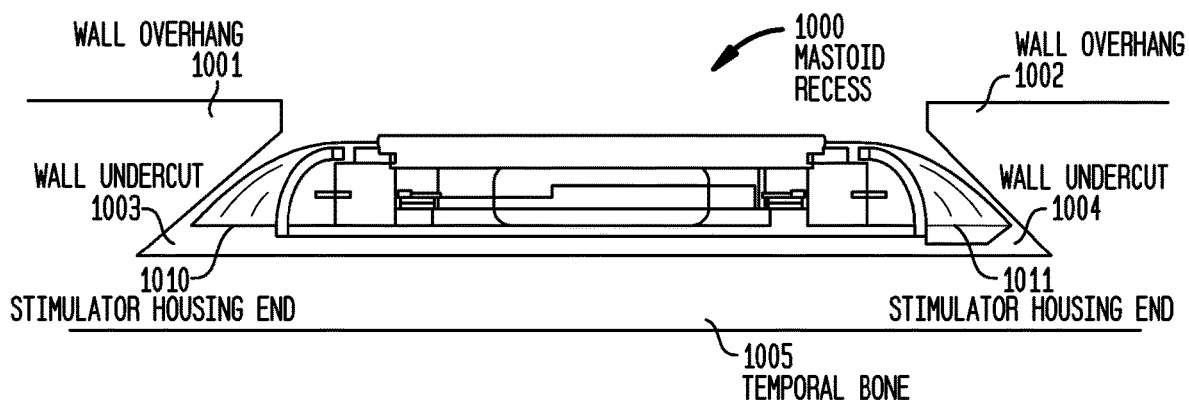
FIG. 10A illustrates a cross section of a stimulator unit housing in a boney recess of a temporal bone with a tapered undercut, in accordance with embodiments of the present technology.
Figure 10B:
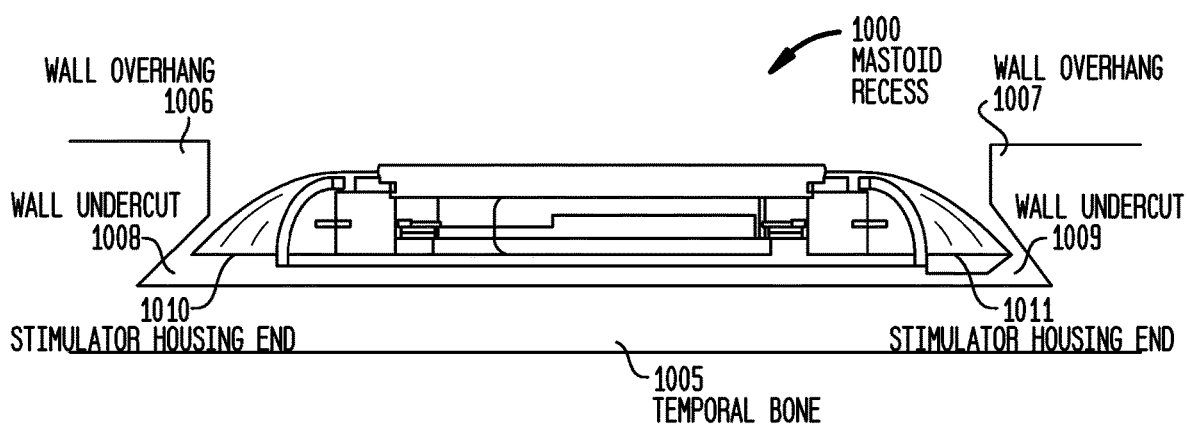
FIG. 10B illustrates a cross section of a stimulator unit housing in a boney recess of a temporal bone with a shorter tapered undercut than the embodiment of the present technology of FIG. 10A.

FIGS. 10A and 10B (collectively, FIG. 10) illustrate another exemplary method of implementing embodiments of the present technology into a recipient. FIG. 10 illustrates a cross section of a stimulator unit housing in a boney recess of a temporal bone with a tapered undercut, in accordance with embodiments of the present technology. More specifically, FIG. 10 illustrates implantable component 200 implanted within a recess of the recipient. FIG. 10A illustrates recipient recess 1000 which comprises recess wall overhangs 1001, 1002 and recess wall undercuts 1003, 1004. A recess drilled by a surgeon preparing to implant, for example, implantable device 200 into a recipient's head, will include side walls. Wall undercuts 1003, 1004 are formed from the drilling of side walls of recess 1000 that taper inwards into temporal bone 1005 of the recipient. FIG. 10A also illustrates implantable component 200, which includes stimulator housing 225. As noted, the four walls of stimulator housing 225 are generally not perpendicular to top surface 201 or bottom surface 210. Instead, walls 202, 203, 204, 205 of stimulator housing 225 are generally slanted upward and inward towards the center of top surface 201, and are generally slanted downward and outward towards the center of bottom surface 210, as shown in FIG. 2. In other words, walls 202, 203, 204, 205 form acute angles with bottom surface 210, forming ends 1010 and 1011, and form obtuse angles (or, if rounded, concave corners) with top surface 201. When the surgeon places implantable component 200 into recess 1000, ends 1010, 1011 fit into wall undercuts 1003, 1004 because ends 1010, 1011 have a similar shape as wall undercuts 1003, 1004. As such, wall overhangs 1001, 1002 hang over ends 1010, 1011 of stimulator housing 225.

As illustrated in FIG. 10B, wall undercuts 1008, 1009 are similar to wall undercuts 1003, 1004 of FIG. 10A, but wall undercuts 1008, 1009 are more shallow than wall undercuts 1003, 1004.

Implanting ends 1010, 1011 of stimulator housing 225 within wall undercuts 1003, 1004 or 1008, 1009 and underneath wall overhangs 1001, 1002 or 1006, 1007 helps prevent unwanted migration and allows for quicker osseointegration of the implantable device into the recess in the recipient's head. Recess 1000 also requires less bone to be removed from the temporal bone, allowing for drilling of recess 1000 to be faster than other procedures. Recess 1000 locks implantable device 200 into place, preventing upwards movement of the device. More specifically, overhangs 1001, 1002 or 1006, 1007 prevent implantable component 200 from lifting off the surface of the recess in a direction away from the recipient's head. Migration of implantable component 200 after implantation, whether along the surface of the recipient's head or in a direction normal to the recipient's head, would put unnecessary stress on electrode leads 150. Such stress on electrode leads 150 may cause electrode leads 150 to break or otherwise damage implantable component 200, such as stimulator/receiver unit 120, connected to the leads. Stress on electrode leads 150 may also damage the implantation of electrode assembly 118 implanted inside the cochlea of the recipient. Such stress may cause electrode assembly 118 to become dislodged from the recipient's cochlea or damage the cochlea. Furthermore, wall undercuts 1003, 1004 and 1008, 1009 prevent "protrusion" of implantable component 200 through the skin after surgery. More specifically, wall overhangs 1001, 1002 and 1006, 1007 are slanted at an angle that is similar to the angle at which walls 202 and 204 are slanted. Therefore, ends 1010, 1011 may rest inside wall undercuts 1003, 1004 and 1008, 1009, but may not dig into the recipient's skin because ends 1010, 1011 will press up against wall overhangs 1001, 1002 and 1006, 1007. At the same time, because wall undercuts 1003, 1004 and 1008, 1009 are shaped similarly to ends 1010, 1011, ends 1010, 1011 should not dig into the recipient's skin even if ends 1010, 1011 have a sharp surface.

As noted, FIGS. 6A and 6B illustrate the implantation of multiple implantable components in the head of a recipient. Migration of one or more of implantable components 200 may also lead to device complications, such as, for example, severing of the connection between the multiple implants or other damage to the leads connecting the implants to each other or to other devices.

When embodiments of the present technology are implemented with a trapezoid shaped boney recess, fixation pins and/or undercut walls, the implantable component will benefit from superior resistance to impact and surgical fixation due to the implantable component's deep integration into the recess and other components helping to fix the implantable component in place.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable housing, comprising:
  a first surface,
  a second surface that is substantially parallel to the first surface;

a plurality of walls joining the first surface to the second surface, wherein the plurality of walls comprises at least a first wall and a second wall;

a first aperture located in the first wall, wherein a first feedthrough is disposed in the first aperture; and a second aperture located in the second wall, wherein a second feedthrough is disposed in the second aperture, wherein the second wall is different from the first wall, and the first wall and the second wall are not parallel to one another.

2. The implantable housing of claim 1, wherein the plurality of walls comprises the first wall, the second wall, a third wall that connects a first end of the first wall to a first end of the second wall, and a fourth wall that connects a second end of the first wall to a second end of the second wall.

3. The implantable housing of claim 2, wherein the first wall and the second wall each connect to the third wall with an obtuse angle and each connect to the fourth wall with an acute angle.

4. The implantable housing of claim 2, wherein the first wall, the second wall, the third wall, and the fourth wall each comprise a convex surface extending from an interior of the implantable housing.

5. The implantable housing of claim 2, wherein the third wall defines a third aperture, and wherein the implantable housing comprises a third feedthrough disposed in the third aperture.

6. The implantable housing of claim 2, wherein the third wall and the fourth wall are each substantially perpendicular to the first surface and the second surface.

7. The implantable housing of claim 1, wherein the first feedthrough and the second feedthrough each comprise a plurality of pins disposed substantially parallel to the first surface and the second surface.

8. The implantable housing of claim 1, wherein the first feedthrough and the second feedthrough are not parallel or perpendicular to one another.

9. An implantable component, comprising:

an implantable housing having a trapezoidal shape comprising a first surface, a second surface substantially parallel to the first surface, and a plurality of walls, wherein the plurality of walls joins the first surface to the second surface and includes a first wall, a second wall, a third wall, and a fourth wall, a first feedthrough disposed in the first wall; and a second feedthrough disposed in the second wall.

10. The implantable component of claim 9, further comprising:

an electrode assembly comprising a plurality of electrodes, wherein a first subset of the plurality of electrodes is electrically connected to the first feedthrough and a second subset of the plurality of electrodes is electrically connected to the second feedthrough.

11. The implantable component of claim 9, further comprising:

a first electrode lead electrically coupled to the first feedthrough and extending along the first wall; and a second electrode lead electrically coupled to the second feedthrough and extending along a portion of the second wall.

12. The implantable component of claim 11, further comprising:

an overmoulding covering the implantable housing, wherein the overmoulding defines an overmoulding opening proximate the third wall, wherein the first electrode lead and the second electrode lead converge proximate the third wall and extend through the overmoulding opening.

13. The implantable component of claim 9, wherein the first wall and the second wall are not perpendicular to the first surface and the second surface of the implantable housing.

14. The implantable component of claim 9, further comprising:

an induction coil disposed at a second end of the implantable housing adjacent the fourth wall, wherein the induction coil is electrically connected to at least one of the first feedthrough or the second feedthrough.

15. The implantable component of claim 9, wherein each of the plurality of walls is defined by a substantially planar surface, wherein an angle between adjacent walls of the plurality of walls is measured between the substantially planar surfaces, and wherein none of the plurality of walls forms a right angle with an adjacent wall of the plurality of walls.

16. The implantable component of claim 9, wherein the first wall and the second wall are not parallel to one another.

17. The implantable component of claim 9, wherein the first wall and the second wall each connect to the third wall with an obtuse angle and each connect to the fourth wall with an acute angle.

18. An apparatus comprising:

an implantable housing comprising a first surface, a second surface substantially parallel to the first surface, and a plurality of walls joining the first surface to the second surface to form a hermetic enclosure, wherein the plurality of walls includes at least a first wall and a second wall, a first feedthrough extending through the first wall, wherein the first feedthrough comprises a plurality of pins disposed substantially parallel to the first surface and the second surface;

a second feedthrough extending through the second wall, wherein the second feedthrough comprises a plurality of pins disposed substantially parallel to the first surface and the second surface;

a stimulator unit disposed in the implantable housing; and an electrode assembly electrically connected to the stimulator unit via both the first feedthrough and the second feedthrough, wherein the first feedthrough and the second feedthrough are not parallel or perpendicular to one another.

19. The apparatus of claim 18, wherein the electrode assembly comprises a bifurcated electrode assembly having a first lead comprising a first plurality of electrodes and a second lead comprising a second plurality of electrodes, wherein the first plurality of electrodes is electrically coupled to the first feedthrough and the second plurality of electrodes is electrically coupled to the second feedthrough.

* * * * *